Figure 1:
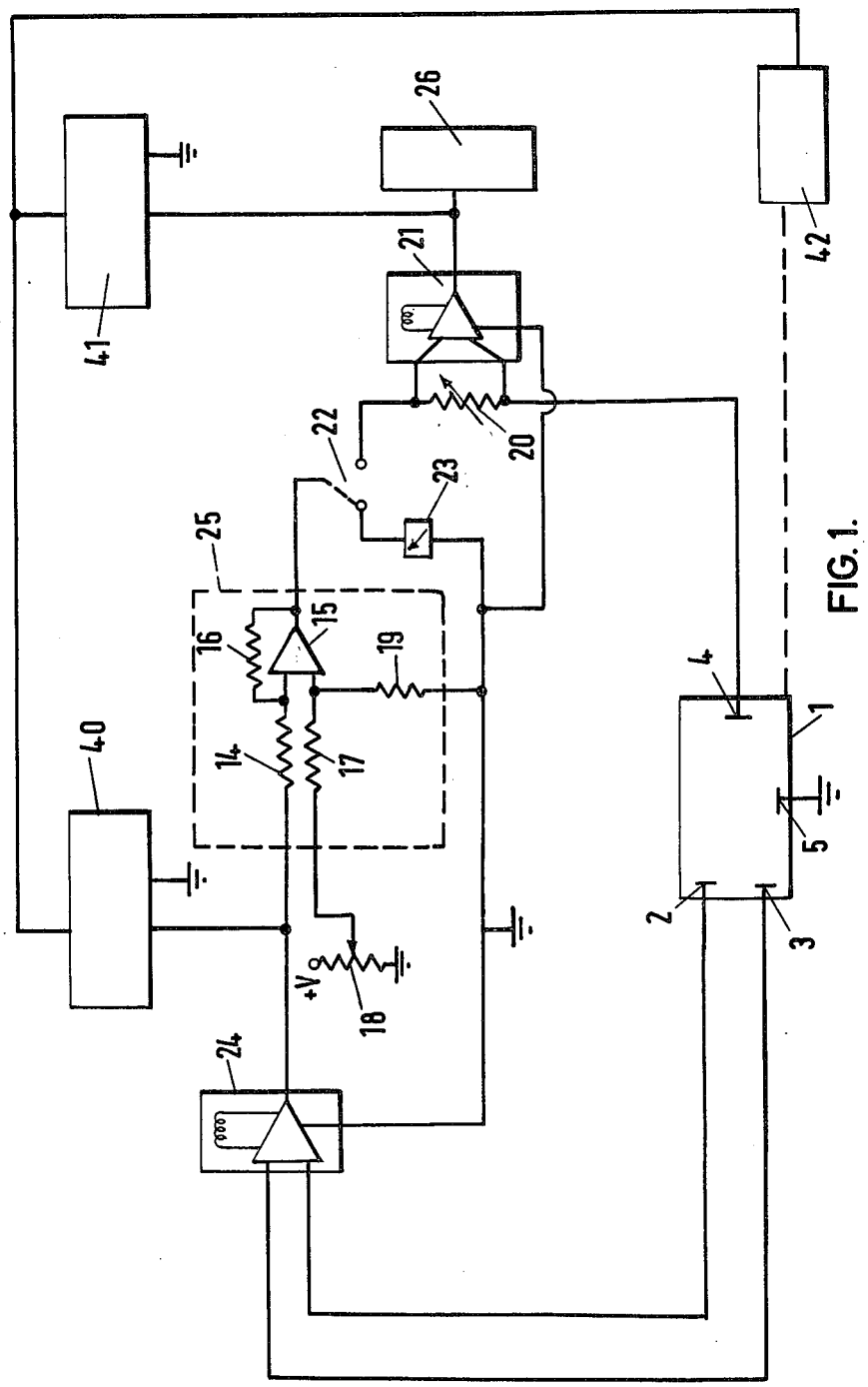

United States Patent [19] [11] 4,111,776
Mansfield [45] Sep. 5, 1978

[54] ANALYTICAL APPARATUS AND PROCESSES

[75] Inventor: John Rickard Mansfield, Middlesbrough, England

[73] Assignee: Imperial Chemical Industries Limited, London, England

[21] Appl. No.: 696,413

[22] Filed: Jun. 15, 1976

[30] Foreign Application Priority Data

Jun. 23, 1975 [GB] United Kingdom ............... 26559/75

[51] Int. Cl.² .......................................... G01N 27/44
[52] U.S. Cl. .................................. 204/195 T; 204/1 T
[58] Field of Search .......................... 204/1 M, 195 T; 23/230 R, 232 E, 253 R, 254 E

[56] References Cited

U.S. PATENT DOCUMENTS

| 2,886,496 | 5/1959 | Eckfeldt | 204/195 T |
| 3,189,533 | 6/1965 | Anscherlik | 204/195 T |
| 3,341,430 | 9/1967 | Wickerham et al. | 204/195 T |
| 3,421,855 | 1/1969 | Kateman et al. | 204/195 T |
| 3,441,490 | 4/1969 | Johansson | 204/195 T |
| 3,563,875 | 2/1971 | Cowlson | 204/195 T |
| 3,647,668 | 3/1972 | Lindblad et al. | 204/195 T |

Primary Examiner—T. Tung
Attorney, Agent, or Firm—Cushman, Darby & Cushman

[57] ABSTRACT

In apparatus for coulometric analysis provision is made for an automatic change of electrolyte in the event of certain forms of analytical failure.

5 Claims, 2 Drawing Figures

ANALYTICAL APPARATUS AND PROCESSES

This invention relates to analytical apparatus and processes, and especially to analytical processes carried out by coulometry.

In the analysis of materials by coulometry a sample may be introduced into an electrolyte and the quantity of a material to be determined which is present in the sample may be found by carrying out in the electrolyte an electrolytic process which consumes the material directly or indirectly; the quantity of electricity passed is a measure of the quantity of material present.

The electrolyte may be a solid or liquid electrolyte. The presence and consumption of materials to be determined may conveniently be sensed for example as a variation in the potential difference between a sensor electrode present in the electrolyte and a reference electrode which is in electrolytic communication with the electrolyte. When this potential difference departs from a desired value a current is passed between a generator electrode which is in the electrolyte and generates a species which consumes the material to be determined and either the reference electrode or an auxiliary electrode which is in electrolytic communication with the electrolyte but prevents species generated at it from reaching the generator electrode. It may be isolated from the generator electrode geometrically, for example, using a porous barrier or membrane. If the current is passed between the generator and the reference electrodes and the species generated at the reference electrode is hydrogen, the reference electrode may suitably be a palladium electrode as this absorbs hydrogen.

This invention comprises apparatus for the coulometric determination of material introduced into an electrolyte in a coulometric cell which apparatus comprises means to sense the presence of the material as a sensing signal and means to pass a sufficient quantity of electricity between a generator electrode in the cell which generator electrode generates a species which consumes the material and is located in the electrolyte and an electrode from which species generated do not reach the generator electrode, to maintain or restore the sensing signal at or to its value when none of the material to be determined is present (the reference value), and means to change the electrolyte in the coulometric cell in response to values of the sensing signal falling outside a pre-determined limit or to a failure to restore the sensing signal to its referance value in accordance with a pre-set operation of the apparatus.

The invention also comprises apparatus as aforesaid together with the coulometric cell.

The invention also comprises a process for the coulometric determination of a material introduced into an electrolyte in which the presence of the material is sensed as a sensing signal and a sufficient quantity of electricity is passed between a generator electrode in the electrolyte which generates a species which consumes the material and an electrode from which species generated do not reach the generating electrode to maintain or restore the sensing signal at or to its value when none of the material to be determined is present (the reference value) and in which the electrolyte is changed in response to values of the sensing signal falling outside a predetermined range or failure to restore the sensing signal to its reference value in accordance with a pre-set operation of the apparatus.

The sensing signal may be produced in response to
 (a) a variation in conductivity of the electrolyte, or
 (b) a variation in the potential difference between a sensor electrode present in the electrolyte and a reference electrode which is in electrolytic communication with the electrolyte, or
 (c) a spectroscopic change in the electrolyte.

The electrode from which species generated do not reach the generator electrode and between which and the generator electrode the aforesaid quantity of electricity is passed may be a reference electrode as aforesaid or an auxiliary electrode which is in electrolytic communication with the electrolyte.

The presence of the material to be determined may, in a preferred form of the invention, be sensed continuously during the addition of the material and it is preferred in this case that the passage of electricity between the generator electrode and the electrode from which species generated do not reach the generator electrode should be such as to maintain a sensing signal at substantially its reference value as, by continuously consuming the material to be determined as it is added, side effects arising from the presence of the said free material in the electrolyte may be avoided.

Apparatus according to the invention is particularly suitable for on-line analyses in chemical manufacturing processes. We have found that replacement of the electrolyte will frequently enable a satisfactory analysis to be carried out in cases where an unreliable coulometric analysis has been obtained. The apparatus serves to carry out an electrolyte change in response to many forms of analytical failure.

The quantity of electricity passing through the generator electrode may suitably be displayed graphically or recorded electronically, for example as an integrated signal displayed in analogue or digital form.

The invention also comprises apparatus for carrying out a process according to the invention which comprises
 (a) a differential to single-ended potential converter having a high input impedence,
 (b) means for feeding (a) with a sensing signal for example the potential difference between the sensor and reference electrodes of a coulometric cell,
 (c) a differential potential input amplifier fed by (a) and by means (for example a potentiometer) for setting the output current of (c) to zero at a desired value of the sensing signal by feeding a suitable off-set potential to (c), the whole apparatus (excluding any coulometric cell) having a phase shift of less than 90° with the input signals received.
 (d) a comparator for comparing a single-ended potential produced by (a) with a pre-set potential, and
 (e) means in response to a signal from (d) indicating a single-ended potential signal from (a) in excess of that pre-set to operate valve gear serving to change the electrolyte in the coulometric cell.

In use, the output of the differential potential input amplifier is fed to the generating electrode of a coulometric cell, of which the auxiliary or reference electrode is earthed. The current passing may suitably be recorded by a high input impedance potentiometric recorder which may suitably be provided in parallel with a variable resistance through which the current to the generator electrode is fed. Conveniently, a switch may be provided to connect the output of the differential potential input amplifier (c) so that it may be switched through a meter to earth to enable the system to be nulled for a given electrode potential in order to avoid generation of a species capable of consuming the material to be determined during a nulling operation prior to the analysis.

One form of the invention will now be described with reference to FIG. 1 which shows a circuit diagram of apparatus according to the invention and FIG. 2 which shows a circuit diagram of modules used in FIG. 1.

A coulometric cell 1 contains a liquid electrolyte, a sensor electrode 2 in the liquid and a reference electrode 3 in communication with the liquid, a generator electrode 4 in the liquid and an auxiliary electrode 5 in electrolytic communication with the liquid, but geometrically isolated from the liquid by a porous barrier (not shown). The sensor electrode is connected to the non-inverting input of an instrumentation amplifier with a field effect transistor input 24 and the reference electrode is connected to the inverting input of the amplifier 6.

The output of amplifier 24 which is of single-ended potential is fed through resistor 14 to the inverting input of operational amplifier 15 of high temperature stability which is provided with a feed-back through resistor 16. The non-inverting input of operational amplifier 15 is fed through resistor 17 with a D.C. potential derived from potentiometer 18 or other D.C. potential reference source and the non-inverting input is also earthed through resistor 19, resistors 17 and 19 together acting as potential dividers. Resistors 14, 17, 19 and 16 cause amplifier 15 to operate in a differential mode.

The output of amplifier 15 is fed through a variable resistor 20 in parallel with a high imput impedance instrumentation amplifier 21 (the output of which is displayed on recorder 26) by means of a switch 22 to generator electrode 4, switch 22 alternatively connecting the output of amplifier 15 through null meter 23 to earth.

Figure 2:
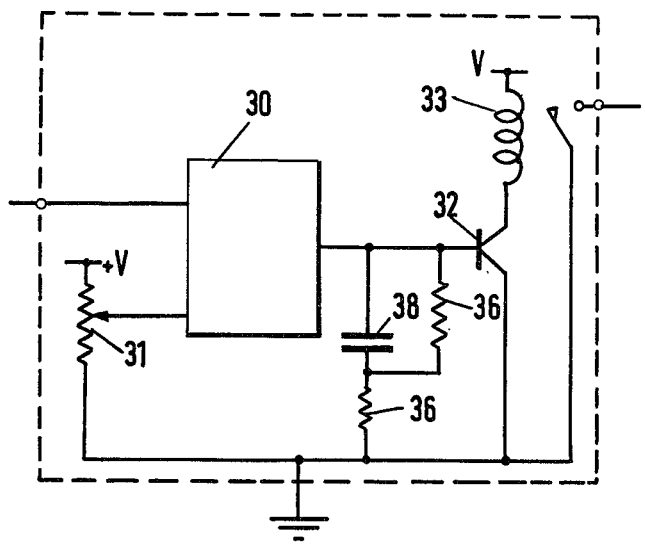

Second connections are taken from the outputs of instrumentation amplifiers 24 and 21 (which are differential to single ended potential converters), respectively to control modules 40 and 41 which are further shown in FIG. 2. The control modules feed electrolyte change module 42 which comprises a cam-timer which, on receipt of a signal from module 40 and/or 41, operates for one cycle operating two valves in sequence, the first serving to drain electrolyte from cell 1 and the second serving to introduce a preset amount of electrolyte to cell 1.

Control modules 40 and 41 are similar in construction and only one is shown in FIG. 2. The signal from the appropriate instrumentation amplifier is fed to comparator 30 to which is also fed an adjustable potential from potentiometer 31. The output of comparator 30 is fed to the base of a switching transistor 32, a leak to earth being provided through resistors 36 and 37, the first of which is in parallel with a capacitor 38. Transistor 32 controls the flow the current through normally open relay 33.

In use switch 22 is adjusted to connect the output of amplifier 15 through null meter 23 to earth and a sufficient potential applied by potentiometer 18 to produce no current. The output of amplifier 15 is then connected to generator electrode 4 and an analysis is commenced. When a sample enters a liquid electrolyte in the coulometric cell the potential difference between the sensor electrode 2 and the reference electrode 3 is altered and this is converted to a single-ended potential at lower impedance in the instrumentation amplifer 24 which causes the differential amplifier 25 to pass current through the generator electrodes so as to bring the sensor electrode to its initial (reference) value.

When the signal from instrumentation amplifier 24 or 21 exceeds the value which is pre-set on the potentiometer in the appropriate comparator a signal is produced which if it persists fro a time sufficient to charge the base of transistor 32 switches transistor 32 to operate relay 33 and thus by means of electrolyte charge module 42 changes the electrolyte in cell 1. If desired an alarm system may be provided to give an alarm if repeated changes of electrolyte do not restore the apparatus to its set mode of operation. Means may also be provided for regular electrolyte changes after specified numbers of analyses in addition to any changes made as aforesaid.

Using the electronic circuit described with reference to the drawing, together with a standard microcoulometric titration cell for sulphur, containing an aqueous electrolyte of 0.5% potassium iodide and 0.4% acetic acid it was possible to determine less than 10 ng of sulphur as sulphur dioxide in a gas stream.

A sulphur analysis was carried out on a microliter sample of a sulphur-containing liquid hydrocarbon, which was pyrolysed in an oxidation furnace using a carrier gas of oxygen and nitrogen to give sulphur dioxide.

The sulphur dioxide containing gas stream was passed into the coulometric titration cell where it reacted with iodine. The current required to regenerate the iodine was directly proportional to the sulphur in the hydrocarbon sample.

We have found that the apparatus can be made to resolve variation in cell potential differences of 1 millivolt or less and to resolve currents of less than 1 microamp.

I claim:

1. Apparatus for the coulometric determination of a material present in successive samples which are introduced into the same batch of an electrolyte which is held in a coulometric cell, which cell comprises a generator electrode, which generator electrode generates a species which consumes the material and is located in the electrolyte, and a second electrode from which species generated do not reach the generator electrode, which apparatus comprises means to sense the presence of the material as a sensing signal and means to pass a sufficient quantity of electricity between the generator electrode and said second electrode to maintain or restore the sensing signal at or to its value when none of the material to be determined is present, said means to sense including a sensor electrode and a reference electrode, means to change the electrolyte in the coulometric cell in response to values of the sensing signal falling outside a predetermined limit, and control means for controlling said means to change including:
   (a) a differential to potential signal convertor having a high input impedance;
   (b) means for feeding (a) with a sensing signal which varies as the potential difference between the sensor and reference electrodes;
   (c) a differential potential input amplifier fed by (a) and by means for setting the output current of (c) to zero at a desired value of the sensing signal by feeding a suitable off-set potential to (c), the whole apparatus excluding the coulometric cell having a phase shift of less than 90° with the input signals received;

(d) a comparator for comparing a potential signal produced by (a) with a pre-set potential; and (e) means in response to a signal from (d) indicating a potential signal from (a) in excess of that pre-set to operate means for changing the electrolyte in the coulometric cell.

2. Apparatus as claimed in claim 1 in which a switch is provided to indicate the output of the differential potential input amplifier (c) so that it may be switched through a meter to earth to enable the system to be nulled for a given electrode potential in order to avoid generation of a species capable of consuming the material to be determined during a nulling operation prior to the analysis.

3. Apparatus for the coulometric determination of a material present in successive samples which are introduced into the same batch of an electrolyte which is held in a coulometric cell which cell comprises a generator electrode, which generator electrode generates a species which consumes the material and is located in the electrolyte, and a second electrode from which species generated do not reach the generator electrode, which apparatus comprises means to sense the presence of the material as a sensing signal and means to pass a sufficient quantity of electricity between the generator electrode and said second electrode to maintain or restore the sensing signal at or to its value when none of the material to be determined is present, and means to change the electrolyte in the coulometric cell in response to a failure to restore the sensing signal to a reference value in accordance with a pre-set operation of the apparatus.

4. Apparatus according to claim 3 wherein said means to sense include a sensor electrode and a reference electrode and which further comprises:

(a) a differential to potential signal convertor having a high input impedance, (b) means for feeding (a) with a sensing signal which varies as the potential difference between the sensor and reference electrodes, (c) a differential potential input amplifier fed by (a) and by means for setting the output current of (c) to zero at a desired value of the sensing signal by feeding a suitable off-set potential to (c), the whole apparatus excluding the coulometric cell having a phase shift of less than 90° with the imput signals received, (d) a comparator for comparing a potential signal produced by (a) with a pre-set potential, and (e) means in response to a signal from (d) indicating a potential signal from (a) in excess of that pre-set to operate means for changing the electrolyte in the coulometric cell.

5. Apparatus as in claim 3 in which a switch is provided to indicate the output of the differential potential input amplifier (c) so that it may be switched through a meter to earth to enable the system to be nulled for a given electrode potential in order to avoid generation of a species capable of consuming the material to be determined during a nulling operation prior to the analysis.

* * * * *